United States Patent [19]

Hare

[11] 3,933,430

[45] Jan. 20, 1976

[54] CONSTANT FLOW SYSTEM FOR DETECTION OF AMINO ACIDS

[75] Inventor: Peter Edgar Hare, Takoma Park, Md.

[73] Assignee: Durrum Instrument Corporation, Palo Alto, Calif.

[22] Filed: June 25, 1975

[21] Appl. No.: 590,216

[52] U.S. Cl. .......... 23/230 R; 23/230 M; 23/230 B; 23/253 R; 73/61.1 C
[51] Int. Cl.² ................. G01N 31/08; G01N 21/26
[58] Field of Search ............... 23/253 R, 259, 230 R, 230 M; 73/61.1 C

[56] References Cited
UNITED STATES PATENTS
3,484,170 12/1969 Smythe et al. .................... 23/253 X
3,551,107 12/1970 Hrdina ............................. 23/253 X OTHER PUBLICATIONS
Eveleigh et al., "An Automated Amino Acid Analysis System," Technicon Symposia, 1967, Vol. I, pp. 311–319.
St. John, "New Method for Probine and Hydroxyproline Extends Usefulness of Fluorometric Amino Acid Analysis," Aminco Lab. News Vol. 31, No. 1, Spring 1975, pp. 1 & 2.

Primary Examiner—R. E. Serwin
Attorney, Agent, or Firm—Flehr, Hohbach, Test, Albritton & Herbert

[57] ABSTRACT

A method and apparatus for the detection of primary and secondary amino acids in a known sequence in a liquid sample stream. The amino acids are rendered detectable by reaction with a fluorometric reagent such as fluorescamine. A conversion reagent, e.g., N-chlorosuccinimide, is added to the sample streams only when secondary amine is present. Baseline shift in the fluorometric detection is avoided by adding an inert liquid diluent stream to the sample stream at a predetermined flow rate at all times except when the conversion reagent is added. By maintaining the diluent and N-chlorosuccinimide streams under constant pressure and synchronously switching between streams to coincide with the presence of a primary or secondary amino acid, liquid flow through the fluorometer is maintained at a substantially constant rate throughout the run.

11 Claims, 2 Drawing Figures

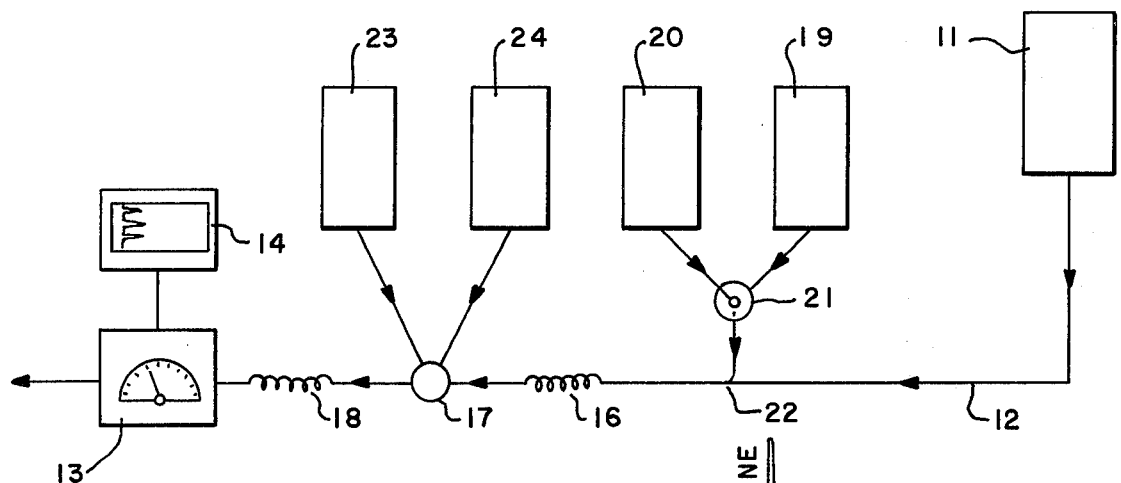
FIG.—1
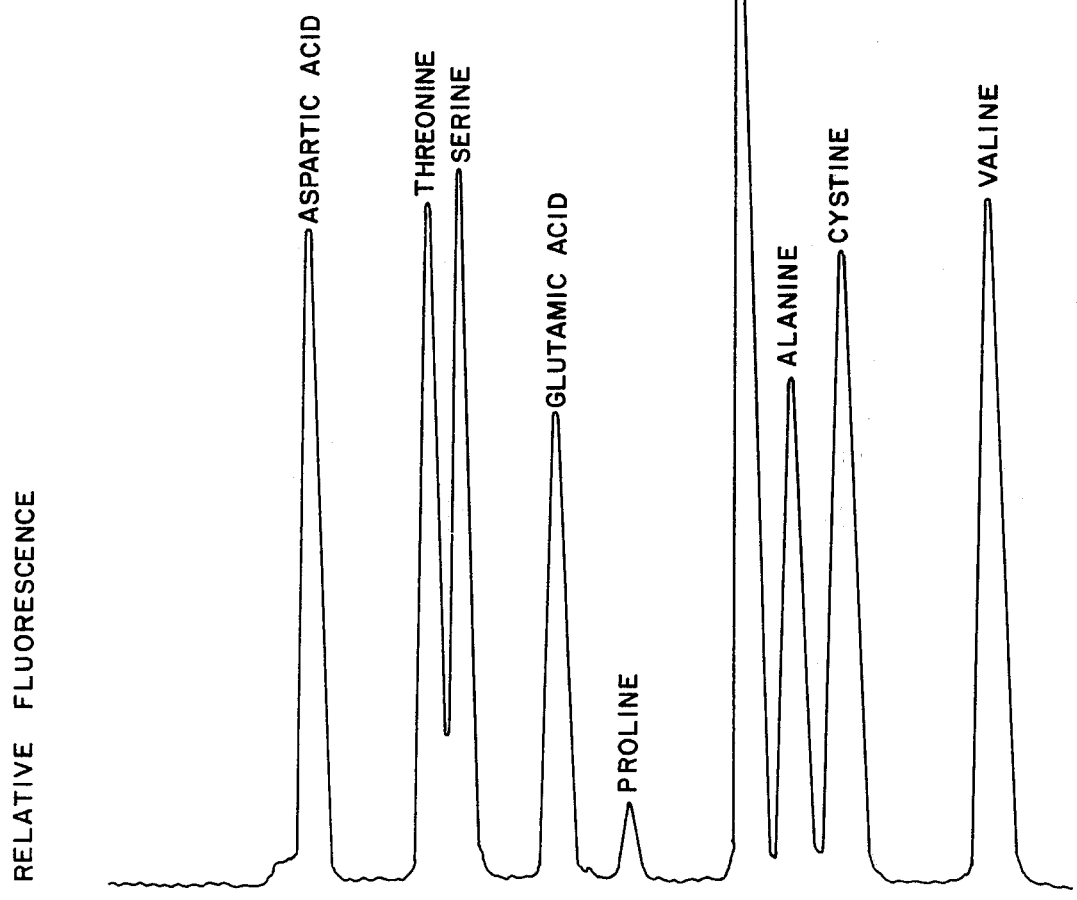
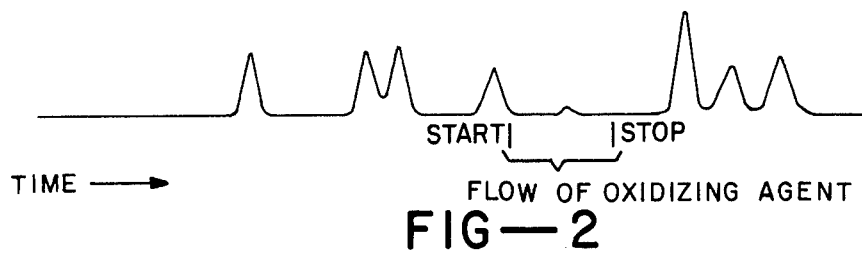
FIG—2

CONSTANT FLOW SYSTEM FOR DETECTION OF AMINO ACIDS

BACKGROUND OF THE INVENTION

Fluorometric analysis has been performed for the detection of primary and secondary amino acids from a single column. One such system is described in a paper by Felix and Terkelsen, entitled "Total Fluorometric Amino Acid Analysis using Fluorescamine," Archives of Biochemistry and Biophysics, Vol. 157, No. 1, July 1973. The same system is described in a paper by the same authors entitled "Determination of Hydroxyproline in Fluorometric Amino Acid Analysis with Fluorescamine," Analytical Biochemistry, Vol. 56, No. 2, December 1973, p. 610. In the above Felix et al articles, standard amino acid mixtures are eluted from a chromotographic column by the use of standard buffer solutions. Fluorescamine is added to the solution prior to passage through the fluorometer. When the sample stream contains secondary amino acid, an oxidizing agent, N-chlorosuccinimide (herein NCS) is added to the sample stream prior to reaction with the fluorescamine. This converts the secondary amino acid to a form which is detectable by the fluorometer upon reaction with the fluorescamine.

The secondary amino acids, e.g. proline and 4-hydroxyproline, of the sequentially eluted sample stream must be converted to another form to be rendered detectable by reaction with conventional fluorogens, e. g., fluorescamine or O-phthalaldehyde. One conversion technique is reaction with an oxidizing agent, N-chlorosuccinimide, as illustrated in the above Felix et al articles. However, the oxidizing agent is known to adversely affect the quantitative detection of the primary amino acids in the stream. Thus, the oxidizing agent conventionally is added to the reagent stream only when the secondary amino acid is present by "pulsing" the oxidizing agent into the stream at that time.

A disadvantage of the above system is that the pulsing causes a sudden increase in the flow rate of liquid through the fluorometer. In turn, this causes a marked "baseline" shift in the recorded chromatograms as illustrated in the foregoing papers. Complex electronics is required to compensate for this baseline shift which is the cause of potential analytical error, as by failure to properly compensate for the pulse in the calibration. The same problem is inherent in other fluorometric detection systems in which an oxidizing agent is pulsed during the presence of only a secondary amino acid.

SUMMARY OF THE INVENTION AND OBJECTS

It is a general object of the invention to provide a system for avoiding baseline shift in the detection of substances in a known sequence in a sample stream in which detection of one of the substances is impeded by reaction with a reagent and detectability of the second substance is improved by reaction with same reagent.

It is a particular object of the invention to provide a system of the foregoing type which avoids baseline shift in the fluorometric detection of primary and secondary amino acids in a known sequence wherein only the secondary amino acid is reacted with an oxidizing agent to render it detectable upon reaction with the fluorometric reagent.

In accordance with the above objects, the present method includes the addition of an inert diluent stream at a predetermined flow rate to the sample stream when the flow path includes the first substance. When the sample stream includes the second substance, the conversion reagent is added at essentially the same flow rate as the liquid diluent stream which is simultaneously discontinued. In this manner, liquid flows through the detection zone at a substantially constant rate to avoid baseline shift. Downstream from the above location, a detection reagent is added which is capable of quantitatively reacting with the first and second substances at that point in the stream to render them detectable. Then, the stream is passed at a constant flow rate through a suitable detector.

For simplicity of description, the present invention will be described with respect to preferred embodiment in which the first substance is a primary amino acid, the second substance is a secondary amino acid, the conversion reagent is an oxidizing agent, and the detection reagent is a fluorogenic reagent.

The apparatus of the present invention is particularly adapted for carrying out the above process. It includes a source of the above liquid sample, a source of oxidizing agent under a predetermined pressure, a source of inert diluent under essentially the same pumping pressure, a fluorometer, and a process line connecting the sample stream source and detector means. Switch valve means is provided for communicating with the liquid diluent and conversion reagent at the inlet side and with the process line at its outlet side. Such valve means is capable of synchronously alternating flow in the process line between liquid diluent and conversion reagent. For fluorometry, a fluorogenic agent source is connected to the process line downstream from the valve means.

BRIEF DESCRIPTION OF THE DRAWINGS

FIG. 1 is a schematic representation of apparatus suitable for carrying out the process of the present invention.

FIG. 2 illustrates chromatograms of a system for detecting primary and secondary amino acids from a single sequential sample without a baseline shift.

DETAILED DESCRIPTION OF THE PREFERRED EMBODIMENT

Briefly described, the present system includes the detection of at least a first and second substance in a known sequence in a liquid sample stream in which detectability of the first substance is impeded by reaction with a conversion reagent and detectability of the second substance is improved by reaction with the same conversion reagent. To simplify the description, the present process will be described with primary and secondary amino acids as the first and second substances and an oxidizing agent as the conversion reagent. More specifically, it will be described in the environment of fluorometry.

Referring to the present system, a conventional mixture of primary and secondary amino acids are supplied with standard buffer solutions to chromatographic column 11 under constant pressure to provide a selected flow rate through the column. The amino acids are eluted in sequence from the column to form the sample stream. It is directed at a constant flow rate through process line 12 to fluorometric detector 13 of a conventional type connected to a recorder 14. Time delay coils 16 and 18 are provided in line 12 to allow sufficient residence time for purposes set forth hereinafter.

A pressurized source 19 of conversion reagent 19 for the secondary amino acid and a pressurized source 20 of an inert liquid diluent, e.g., water, are connected to common switch valve means 21 which is in turn connected to line 12 at a selected location 22.

Valve means 21 include a first position in which liquid flows only from source 19 and a second position in which liquid flows only from source 20. Valve means 21 synchronously alternates from flow into process line 12 from sources 19 or 20 by external manual or automatic control means, not shown.

Any other valve means which performs the above function of switching between sources 19 and 20 may be employed. For example, separate on-off valves flowing through a common manifold with a synchronous switch may also be employed.

Sources 19 and 20 are maintained at essentially the same back pressure so that the flow of liquid through valve means 21 is essentially constant when liquid is supplied through either of sources 19 or 20. One means for creating uniform back pressure is by the use of a gas, e.g., air, from a common source. Alternatively, the uniform back pressure may be created by a common pump to both reservoirs.

A source of fluorogenic detection reagent is supplied at a uniform flow rate through four-way manifold 17 to process line 12. Uniformity of flow rate may be maintained by controlled constant back pressure as set forth above. If the fluorogenic agent is of the type that requires an alkaline pH for detection, such as fluorescamine, an alkaline buffer solution is supplied at a constant flow rate to the system from pressurized buffer source 24 to line 12 through manifold 17.

Referring to the present process, a continuous method for the detection of primary and secondary amino acids in known sequence in a liquid sample is carried out while avoiding a baseline shift in the recorded chromatogram. A mixture of primary and secondary amino acids are eluted from chromatographic column 11 in sequence at a constant flow rate. In a standard mixture of amino acids, the primary amino acids constitute the first four amino acids to be eluted. During passage of such amino acids through location 22, the inert liquid diluent flows at a constant rate through valve means 21 and into line 12. This is accomplished by maintaining a constant pressure as set forth above. The sample stream is then buffered to an alkaline pH from a suitable buffer (e.g., lithium borate), from source 24 through manifold 17, if required for the particular fluorogenic reagent. The fluorogenic reagent, e.g., fluorescamine, is directed continuously through manifold 17 into line 12 from source 23. Time delay coil 18 provides sufficient residence time for completion of the reaction between the amino acids and fluorescamine. Then, the sample stream passes through fluorometer 13 and the results are recorded as a chromatogram by recorder 14.

Immediately prior to the passage of the first secondary amino acid in the sample stream, typically proline, valve means 21 is actuated to shift from inert diluent source 20 to oxidizing agent source 19. In this manner, the oxidizing agent is simultaneously substituted for the discontinued liquid diluent stream.

Reaction coil 16 provides sufficient residence time for oxidation of the proline with the oxidizing agent supplied from source 19.

After passage of the secondary amino acid, proline, valve means 21 is again switched to its original position so that the flow of NCS is discontinued and the flow of inert liquid diluent is reinstituted.

It is apparent that in the above system, constant flow rate of liquid passes the detection zone of fluorometer 13. Thus, there is no baseline shift in the recorded chromatogram.

The system of the present invention is applicable to other sample streams containing first and second substances in which detectability of one substance is impeded by reaction with a conversion reagent and detectability of the other substance is improved by reaction with the same conversion reagent. More specifically, it is also applicable to other fluorometric detection systems for the determination of primary and secondary amino acids. Such systems include the use of other fluorogenic reagents such as O-phthalaldehyde and other oxidizing or conversion reagents. In certain detection systems, it may not be necessary to utilize the buffer from source 24.

In order to more clearly disclose the nature of the present invention, a specific example of the practice thereof is hereinafter given. It should be understood, however, that this is done by way of example and is intended to neither delineate the scope of the present invention nor limit the appended claims.

Example 1

A sample comprising a standard calibration mixture of the nine amino acids illustrated in FIGS. 2 and 3 is run through a 2 × 30 cm chromatographic column 11 filled with DC-4A cation exchange resin (Durrum Chemical Corp., Palo Alto, Calif.). A buffer solution comprising 0.2 N sodium citrate with a pH value of 3.25 is forced under pressure through the column to elute the sample stream at a constant flow rate of 6 ml/hr. For this purpose, the column is pressurized from an air reservoir at 400 psi. As illustrated in FIG. 2 and 3, the first four amino acids eluted from the column are the primary amino acids, aspartic acid, threonine, serine and glutamic acid. Diluent, water, is supplied from source 20 pressurized at 100 psi through valve 21 at a flow rate of 6 ml/hr during this stage of elution. At a time just prior to the flow of secondary amino acid, proline, past location 22, valve means 21 is actuated to shift the flow of liquid from water (source 20) to oxidizing agent, comprising $10^{-3}$M NCS in water (source 19). The time of this shift is designated "start" on the time line of the chromatograms of FIGS. 2 and 3. Source 19 is maintained under the same pressure (100 psi) as the water to provide the same flow rate (6 ml/hr.). Time delay coil 16 is 10 feet long to provide an approximate residence time of 30 seconds, sufficient for oxidation of the secondary amino acids. Time delay coil 18 is 30 feet long to provide the same residence time for reaction of the fluorescamine and amino acids.

Fluorogenic reagent is supplied continuously from source 23 maintained under 50 psi pressure to provide a flow rate of 3 ml/hr. This stream comprises fluorescamine at a concentration of 30 mg/100 ml of acetone. Fluorometer 13 is of the type sold under the trademark "Fluoromonitor" by American Instrument Co., Silver Spring, Md.

After passage of the proline at the time designated "stop" on the time line of FIGS. 2 and 3, valve means 21 is actuated to discontinue NCS flow from source 19 and to reinstitute water flow from source 20 at the same flow rate as in the original system. The remainder of the amino acids illustrated in FIGS. 2 and 3 in order of elution are glycine, alanine, cystine, and valine. The two chromatograms were formed simultaneously with the more sensitive run schematically illustrated as the upper run at a sensitivity of 0–10 millivolts and the lower run at a sensitivity of 0–100 millivolts. These are recorded simultaneously from the same signal.

What is claimed is:

1. In a continuous method for avoiding baseline shift in the detection of at least a first and second substance in a known sequence in a liquid sample stream moving in a flow path at a substantially constant flow rate to a detection zone, wherein detectability of said first substance is impeded by reaction with a conversion reagent and detectability of said second substance is improved by reaction with said conversion reagent, the steps of
   a. adding an inert liquid diluent stream at a predetermined flow rate to said sample stream in said flow path when the sample stream includes said first substance at a selected location in said flow path,
   b. adding a conversion reagent stream at essentially the same flow rate as the liquid diluent stream of step (a) at said selected location when the sample stream at said location includes said second substance and simultaneously discontinuing the flow of said liquid diluent stream, whereby liquid flows through said detection zone at a substantially constant rate during detection of said first and second substances.

2. The method of claim 1 together with the step of
   c. continuously adding a detection reagent to the sample stream flowing in said flow path downstream from said selected location, said detection reagent being capable of quantitatively reacting with said first and second substance in said stream to render the same substances detectable.

3. The method of claim 2 in which said first substance is a primary amino acid and said second substance is a secondary amino acid.

4. The method of claim 3 in which said detection reagent is a fluorogenic reagent.

5. The method of claim 3 in which said primary and secondary amino acids are placed into sequence from a mixture of the same to form said sample stream by sequential elution from a chromatographic column.

6. The method of claim 3 in which the conversion reagent is an oxidizing agent.

7. The method of claim 1 in which the inert diluent stream is added to the sample stream at said selected location.

8. The method of claim 4 in which the inert diluent stream and conversion reagent stream are directed through common switch valve means capable of synchronously alternating flow between said streams:

9. The method of claim 1 in which the flow of conversion reagent stream in step (b) is discontinued and the flow of inert diluent is reinstituted when the sample stream at said selected location again includes said first substance.

10. In a system suitable for the determination of a first substance and a second substance in a known sequence in a liquid sample stream while avoiding a baseline shift in a detection zone by maintaining a constant flow rate therethrough,
    a. a source of said liquid sample containing a known sequence of said first and second substances,
    b. a source of liquid conversion reagent under a predetermined pressure, said conversion reagent being capable of improving the detectability of the second substance while impeding detectability of the first substance,
    c. a source of an inert liquid diluent under pressure substantially equal to said predetermined pressure,
    d. detector means,
    e. a process line connecting said sample stream source and detector means,
    f. switch valve means communicating at the inlet side with said liquid diluent source and conversion reagent source and at the outlet side with said process line, said valve means being capable of synchronously alternating flow into said line from said liquid diluent and liquid reagent source.

11. The system of claim 10 together with
    g. a source of detection reagent communicating with said line downstream from said valve means for reacting with said first and second substances to render the same detectable.

* * * * *